(12) United States Patent
Schuetz

(10) Patent No.: US 9,194,520 B2
(45) Date of Patent: Nov. 24, 2015

(54) PLUG CONNECTION

(75) Inventor: Alfred Schuetz, Zollikofen (CH)

(73) Assignee: Mirage Health Group Ltd., Welwyn Garden City (GB)

( * ) Notice: Subject to any disclaimer, the term of this patent is extended or adjusted under 35 U.S.C. 154(b) by 854 days.

(21) Appl. No.: 12/517,535

(22) PCT Filed: Dec. 5, 2007

(86) PCT No.: PCT/EP2007/010570
§ 371 (c)(1),
(2), (4) Date: Feb. 5, 2010

(87) PCT Pub. No.: WO2008/068010
PCT Pub. Date: Jun. 12, 2008

(65) Prior Publication Data
US 2010/0136501 A1  Jun. 3, 2010

(30) Foreign Application Priority Data

Dec. 5, 2006 (DE) .......................... 10 2006 057 613

(51) Int. Cl.
| | |
|---|---|
| *F16L 39/00* | (2006.01) |
| *F16L 37/098* | (2006.01) |
| *A61C 8/00* | (2006.01) |
| *A61M 3/02* | (2006.01) |
| *A61M 39/10* | (2006.01) |

(52) U.S. Cl.
CPC ........... *F16L 37/0982* (2013.01); *A61C 8/0022* (2013.01); *A61M 3/0279* (2013.01); *A61M 39/1011* (2013.01); *F16L 37/0987* (2013.01); *A61M 2039/1027* (2013.01); *A61M 2039/1066* (2013.01); *A61M 2210/0625* (2013.01); *A61M 2210/0662* (2013.01)

(58) Field of Classification Search
USPC .......................... 285/319, 317, 308, 307, 305
See application file for complete search history.

(56) References Cited

U.S. PATENT DOCUMENTS

| 763,317 | A | * | 6/1904 | Nelson ........................... 285/320 |
| 3,826,523 | A | * | 7/1974 | Eschbaugh ..................... 285/39 |
| 3,847,421 | A | * | 11/1974 | Eschbaugh et al. ........... 285/353 |

(Continued)

FOREIGN PATENT DOCUMENTS

| CH | 581 273 | 10/1976 |
| DE | 1 083 497 | 6/1960 |

(Continued)

OTHER PUBLICATIONS

German Search Report w/English Translation.

(Continued)

*Primary Examiner* — Aaron Dunwoody
(74) *Attorney, Agent, or Firm* — Crowell & Moring LLP

(57) ABSTRACT

A releasable plug connection for inserting a nozzle tube into a jack includes a hollow cylinder and a sleeve displaceably mounted on the cylinder. A nozzle tube, forming the hollow cylinder, is provided with radially spring-loaded lugs, the free ends of which are in contact with a locking surface. The locking surface is formed on a flange of the sleeve, which can slide relative to the hollow cylinder against the force of a spring. To release the connection, the sleeve is pushed back so that the lugs are pushed inwardly, and ends of the lugs slide from the locking surface. As soon as the lug ends have left the locking surface, the nozzle tube shoots from the jack under the action of the spring.

11 Claims, 4 Drawing Sheets

(56) References Cited

U.S. PATENT DOCUMENTS

| | | | |
|---|---|---|---|
| 3,851,984 A | | 12/1974 | Crippa |
| 4,105,226 A | * | 8/1978 | Frey et al. ............... 285/148.21 |
| 4,966,398 A | | 10/1990 | Peterson |
| 5,281,137 A | | 1/1994 | Jousson |
| 5,343,892 A | | 9/1994 | Saito |
| 5,489,125 A | * | 2/1996 | Hohmann ...................... 285/81 |
| 6,283,443 B1 | * | 9/2001 | Taneya ...................... 251/149.6 |
| 6,293,792 B1 | | 9/2001 | Hanson |
| 7,284,772 B2 | * | 10/2007 | Alder et al. .................. 285/316 |
| 7,431,346 B2 | * | 10/2008 | Frost et al. ................... 285/317 |

FOREIGN PATENT DOCUMENTS

| | | |
|---|---|---|
| DE | 1 291 056 | 3/1969 |
| DE | 39 04 186 A1 | 8/1990 |
| DE | 41 23 198 A1 | 1/1993 |
| EP | 0 140 995 A2 | 5/1985 |
| WO | WO 01/21118 A1 | 3/2001 |

OTHER PUBLICATIONS

PCT/EP2007/010570 PCT/ISA/210.

* cited by examiner

PLUG CONNECTION

BACKGROUND OF THE INVENTION

The invention relates to a releasable plug connection, which is either in a connected or released state, consisting of two components, namely a jack and a plug, preferably a jack and a nozzle tube connected with a hand part of a dental water jet or an ear syringe, wherein in the connected state the plug is inserted into the jack and held in it by a latch, for the purpose of which the latch is connected with one of the components in a radially spring loaded manner and contacts a locking surface formed on the other component, as a result of which sliding back of the plug out of the jack is prevented.

These types of plug connections are known, wherein the latch, for instance, is formed by a ball set in the plug which, against the force of a compression spring also arranged in the plug, can be radially displaced relative to the plug. When the plug is introduced into the jack, the ball partly engages in a depression in the inner wall of the jack under the force of the compression spring and in this way secures the plug from being unintentionally pulled out because the ball is in contact with a wall of the depression that serves as a locking surface. To release the connection, a pulling force is exerted on the plug in axial direction, whereby the ball is forced back by the ramp-shaped locking surface against the force of the compression spring back into the plug so that the plug can be pulled from the jack again.

Such a plug connection is only safe to a limited extent since the plug can be pulled from the jack by applying a high pulling force. In addition, the plug connection can only be adjusted with difficulty: if the force of the compression spring which presses the ball into the depression is too weak, the plug can be easily, and therefore possibly also inadvertently, pulled out. If it is designed too strong, an excessive removing force must be exerted.

Such a connection is therefore not suited, for instance, for joining the nozzle tube of a dental water jet or an ear syringe to a jack provided on a hand part. Since the nozzle tube is frequently designed as a one-off part, it is particularly important to realize the plug connection so that it is constructed as simple as possible, that it guarantees a secure hold and that it can be released again with a force that does not change from nozzle tube to nozzle tube so that the user of the dental water jet or the ear syringe can become accustomed to the force to be exerted.

SUMMARY OF THE INVENTION

To solve these problems, the invention provides that the locking surface largely extends radially to the longitudinal axis of the jack and plug, as a result of which sliding back of the plug from the jack is prevented even when very high pulling forces are applied. In addition, the other component consists of two sections that can be displaced relative to each other to a limited extent in axial direction, wherein the locking surface is formed on one of the sections and the other section has a contact point for the latch which is arranged so that on pushing together of the sections against the force of a spring acting in axial direction the latch contacts the contact point and is pushed from the locking surface in radial direction by sliding on the contact point.

In this way, it is achieved that the plug connection cannot be released by a pull on the nozzle tube but by the displacement of one of the sections relative to the other against the force of a spring, wherein the displacement force alone is determined by the preload of this spring, which thus can be selected independently of the spring force radially acting on the latch.

The contact point may be a surface of the said section or may be formed by a circumferential edge of said section, which is followed by an inclined surface, the gradient of which is equal to or greater than the acute angle of the latch, allowing the latch to reach its position behind the locking surface.

As already mentioned, the releasable plug connection is used for dental water jets or ear syringes so that the one component is a jack and the other component is a nozzle tube, while the latch is formed by one but more preferably by at least two lugs standing out from the nozzle tube at an acute angle which yield under spring load in radial direction. The nozzle tube is an injection moulded part which, by means of a suitably designed injection mould, can be provided with the lugs so that the production effort for the nozzle tubes is not significantly increased.

Another term used for dental water jet is dental irrigator. Another term used for ear syringe is ear canal irrigator or ear canal irrigation device.

A secure hold of the nozzle tube in the jack is achieved if the ends of the lugs have an end surface which, in the relaxed spring condition of the lugs, extend parallel to the locking surface. This results in that the lugs can be moved from the locking surface alone by generating a transverse force and the nozzle tube can practically not be pulled from the jack by the application of a pulling force which acts vertically to the end surface or the locking surface.

Preferably, the lugs are not formed immediately on to the shaft of the nozzle tube but rather have a web, each radially standing out from the nozzle tube at the end facing the nozzle tube which serves as a stop for the spring arranged between the sections.

To obtain sections that can be displaced relative to each other in axial direction, the jack consists of a hollow cylinder and a sleeve which slides on the hollow cylinder against a stop, wherein the stop defines the greatest longitudinal expansion of the jack and wherein the sleeve has an inwardly directed flange, the side of which facing the hollow cylinder defines the locking surface.

To define the contact with which the lugs are pushed to the inside upon displacement of the sleeve on the hollow cylinder, the hollow cylinder has an inner wall ending in an inclined surface at an end opposite the flange. Preferably, the inclined surface has a frustoconical form.

In addition, the sleeve has a spring stop protruding into the hollow cylinder for the spring acting in axial direction, wherein the distance between the spring stop and the locking surface is smaller than the length of the lugs. As a result, with the nozzle tube not inserted, the spring acts between the hollow cylinder and the sleeve, preloading them at a distance, while, with the nozzle tube inserted, the spring contacts the webs, as a result of which the lug ends are pressed against the locking surface on the sleeve by the spring.

Preferably, extensions originate from the flange in axial direction, wherein the spring stop is formed by the faces of these extensions, each two of which form a guide for each of the lugs.

To support the spring on the hollow cylinder, it is provided that the hollow cylinder has a base on which the spring, co-axially arranged relative to the nozzle tube, is supported. In addition, the base of the hollow cylinder has a central opening through which the nozzle tube protrudes.

The object of the invention is, furthermore, an ear syringe (irrigator) nozzle tube or a dental water jet (irrigator) nozzle tube having a distal end for the discharge of liquid into an ear or for the discharge of liquid into a mouth, respectively, and a proximal end for connection to an ear syringe device or to a dental water jet device, respectively, characterized in that it has one, but more preferable, at least two lugs standing out from the nozzle tube at an acute angle towards the distal end which yield in radial direction under spring load.

Preferably, the nozzle tube has four lugs.

Additional features of the nozzle tube are as follows:

(1) The ends of the lugs have an end surface which, in the relaxed spring state of the lugs, extend largely vertically to the longitudinal axis of the nozzle tube.

(2) The base of each of the lugs is formed by a web radially standing out from the nozzle tube.

(3) The webs form an abutting surface for the spring acting on the sleeve in the connected state of the connection.

(4) The webs are arranged at a distance from the end of the nozzle tube which is provided for insertion into a jack. This allows the proximal end of the nozzle tube to protrude into the opening in the base of the hollow cylinder.

(5) The proximal end of the lugs are coupled to the web at a distance from the body of the nozzle tube. This allows the distal ends of the lugs to reach a negative acute angle with regard to the body of the nozzle tube.

For the purpose of irrigation of an ear, the distal end of the nozzle tube has a diameter which allows insertion of this end into the auditory canal of an ear.

The object of the invention is, furthermore, a jack for a plug connection, characterized in that it consists of a hollow cylinder and a sleeve that can slide on the cylinder against a stop, wherein the stop defines the greatest longitudinal extension of the jack and the sleeve has an inwardly directed flange, the side of which facing the hollow cylinder defines a locking surface, and that the inner diameter of the flange is greater than the inner diameter of the hollow cylinder.

Additionally, the hollow cylinder has a frustoconically ending inner wall at an end facing the flange.

This design allows to release the connection by sliding back the sleeve on the hollow cylinder so that the lugs of a nozzle tube, inserted into the jack as a plug, are pressed inwardly and thereby leave the locking surface.

Additional features of the jack are as follows:

(1) The hollow cylinder has a base which is in contact with a spring and has a central opening.

(2) Extensions originate from the flange in axial direction and a spring stop is formed by the faces of these extensions.

The object of the invention is, furthermore, an ear-syringe with a hand part or a dental water jet with a hand part, respectively, wherein the nozzle tube is releasably connected to the hand part, characterized in that the nozzle tube is formed according to the description of a nozzle tube as given above and that the hand part is provided with a jack according to the description of a jack as given above.

The invention is explained in more detail in the following by means of an embodiment. It shows:

DETAILED DESCRIPTION OF THE INVENTION

Figure 1A:
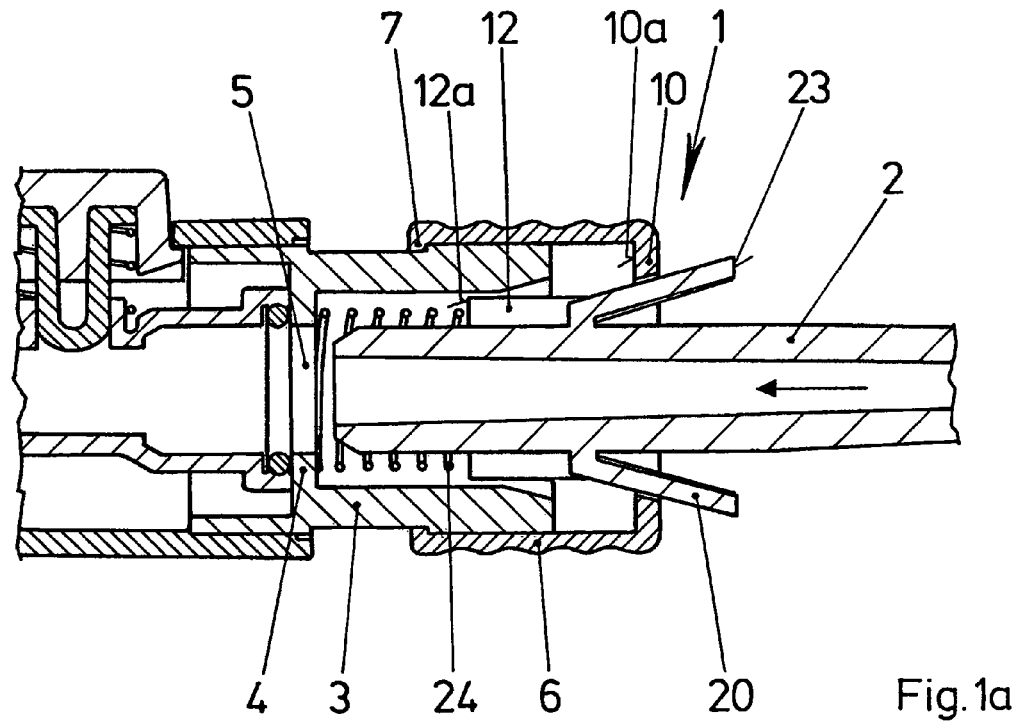
FIG. 1a to 1c is a longitudinal section through a plug connection, wherein the part figures show the sequence upon establishing the plug connection, FIGS. 2a and 2b a longitudinal section through a plug connection, wherein the part figures show the sequence on removing the plug connection, FIG. 3 a perspective representation of a nozzle tube, FIG. 4 a perspective representation of a sleeve for placing on to a hollow cylinder to form a jack.
Figure 1B:
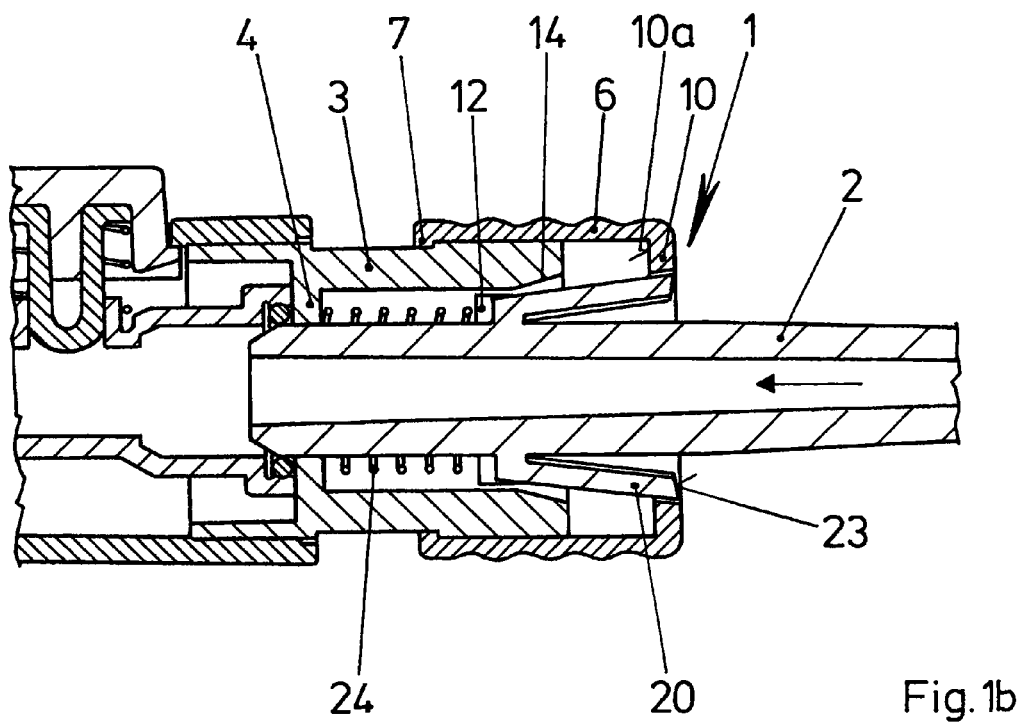
Figure 1C:
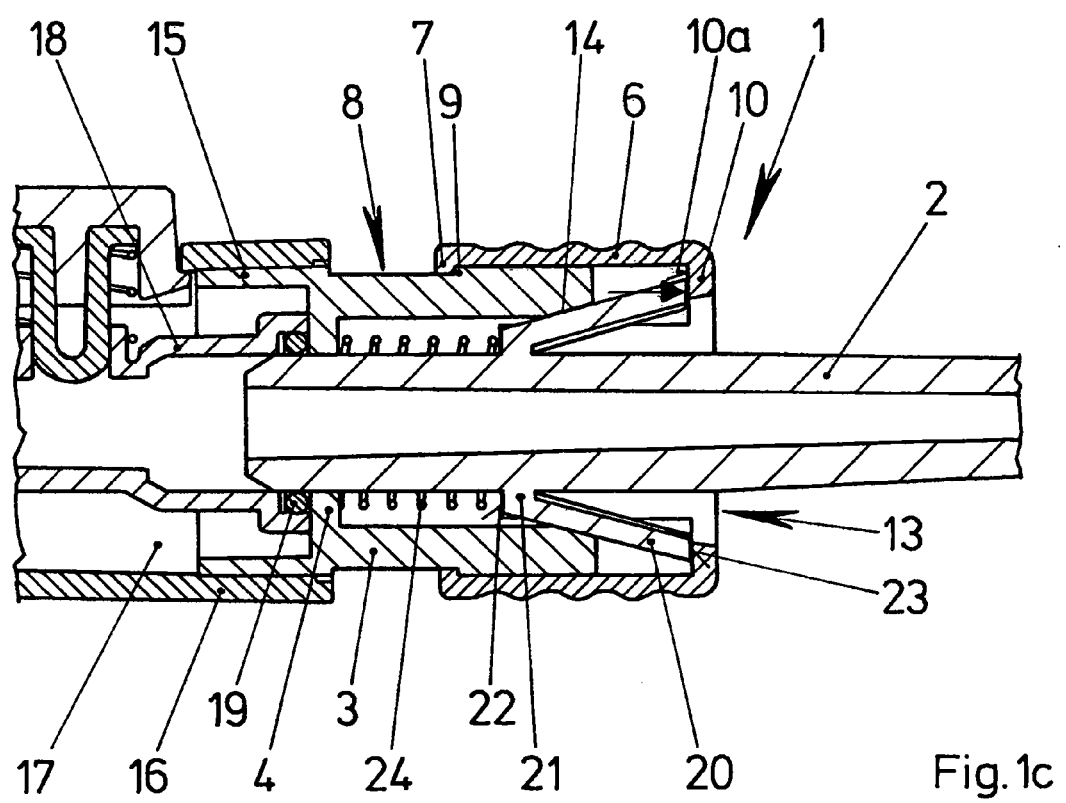

Reference is initially made to FIG. 1c. This shows a jack 1 and a nozzle tube 2 which are joined into a plug connection in that the nozzle tube 2 is inserted into the jack 1 in the way of a plug. The jack 1 consists of a hollow cylinder 3 with a base 4 in which a central opening 5 is located through which the nozzle tube 2 protrudes.

A sleeve 6 is co-axially placed on the hollow cylinder 3. The sleeve, at one end, has a collar 7 facing to the inside which engages in a circumferential flat outer groove 8 on the hollow cylinder. The one flank of the outer groove 8 forms a stop 9 for the collar 7 so that the sleeve 6 can only reach the basic position shown in FIG. 1a to 1c.

Figure 4:
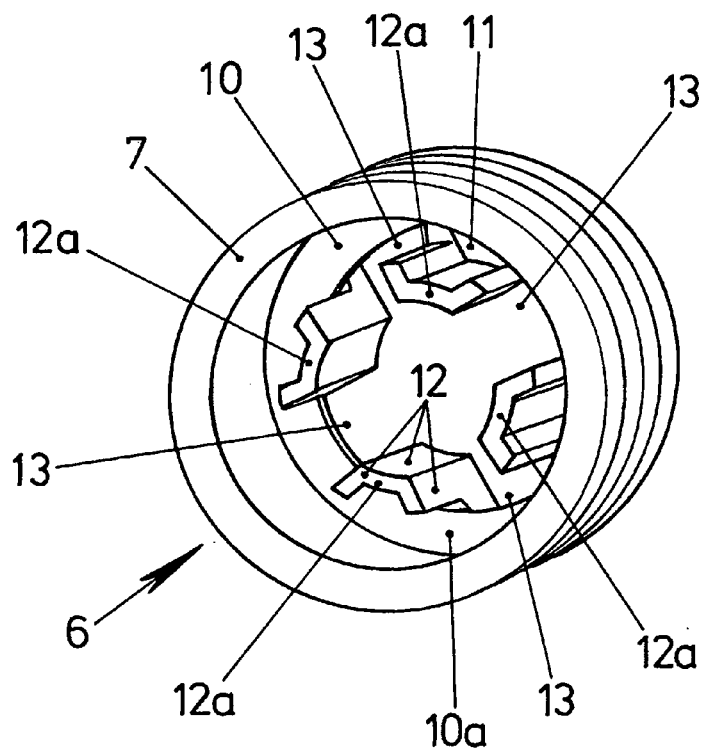

As shown in more detail in FIG. 4, the other end of the sleeve 6, protruding over the hollow cylinder 3, has a flange 10 facing to the inside with a locking surface 10a, the inner diameter of which is greater than the inner diameter of the hollow cylinder 3. As is evident in more detail in FIG. 4, the flange 10 has four trapezoidal protrusions 11 facing to the inside which, between them, each form a rectangular slot in the plane of the flange 10. At the inner edges and the lateral edges of the protrusions 11, walls 12 follow in axial direction which, when connected to a slot each, form a channel 13. Between the walls 12 and the sleeve 6 there is a free space which the hollow cylinder 3 enters. The walls 12 thereby form extensions protruding into the hollow cylinder, the faces 12a of which form a spring stop.

The front end of the hollow cylinder 3 located opposite the flange 10 is designed expanding to the outside on the inside and forms a truncated cone 14, the pitch of which is low and therefore encloses an acute angle with the cylindrical inner lateral area of the hollow cylinder.

On the base 4, a cylindrical extension 15 is formed which stands out in axial direction from the base and which can be inserted in a corresponding accommodation 16 on a hand piece 17. The hand piece 17 has a central tube 18 which contacts the base 4 so that the end of the nozzle tube 2 protruding through the opening 5 in the base 4 is inserted in it. A sealing ring 19 ensures the tightness of the connection.

Figure 3:
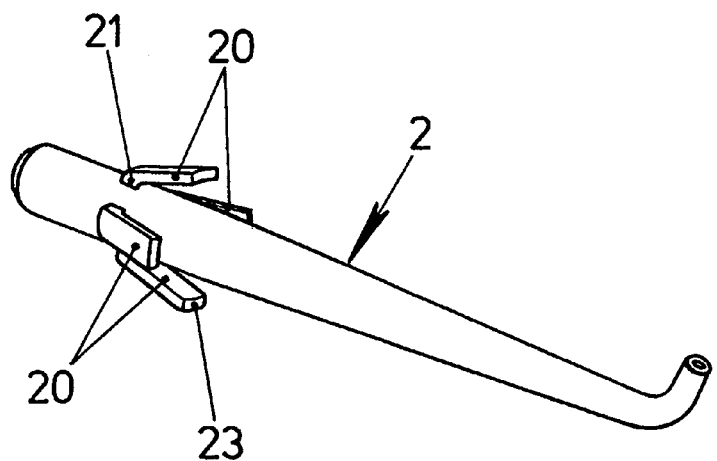

As is shown in more detail in FIG. 3, the nozzle tube 2 has four lugs 20, in the area of the end that is inserted in the jack 1 which faces away from that end, which enclose an acute angle with the lateral surface of the nozzle tube 2, wherein the angle roughly corresponds to the cone angle. Each of the lugs 20 starts at a web 21 standing out from the nozzle tube 2 whose lower side facing away from the lugs 20 represents a radially extending contact surface 22. In their free end, each of the lugs 20 ends in a connection surface 23 which also extends in radial direction.

Within the hollow cylinder, co-axially with the nozzle tube 2, a spring 24 is arranged in the form of a cylindrical spring which on the one hand is supported on the base 4 and on the other hand on the contact surface 22 or the faces 12a of the walls 12. The spring 24 is so designed that it exerts an axial force on the webs 21 of the nozzle tube 2 in the assembly position shown in FIG. 1c.

For inserting and fixing the nozzle tube 2 in the jack 1, the following procedure takes place. The nozzle tube 2 is inserted, according to FIG. 1a, with its end having the lugs 20 into the jack 1 while the lugs 20 are located in the channels 13 where they are guided by the walls 12.

On further insertion of the nozzle tube 2 in the jack 1 according to FIG. 1, the lugs 20 are pushed to the inside by the flange 10 under spring load so that the angle of incidence of the lugs 20 relative to the nozzle tube 2 is reduced. In the process, the spring 24 prevents a displacement of the sleeve 6 since it still contacts the faces 12a of the walls 12.

As soon as the lug ends have passed the flange 10, the lugs snap outward again so that their end surfaces 23 come into contact with the locking surface 10a of the flange 10. Since the webs 21 also have passed the face 12a of the walls 12, the cylindrical spring 24 now contacts the same so that a preload is exerted on the nozzle tube 2 which, by way of the lugs 20, is transmitted to the sleeve 6 which remains in its basic position since it contacts the stop 9 with its collar 7.

The nozzle tube 2 is now fixed in the jack 1 and can therefore no longer be released easily since the lugs 20 engage behind the flange 10.

Figure 2A:
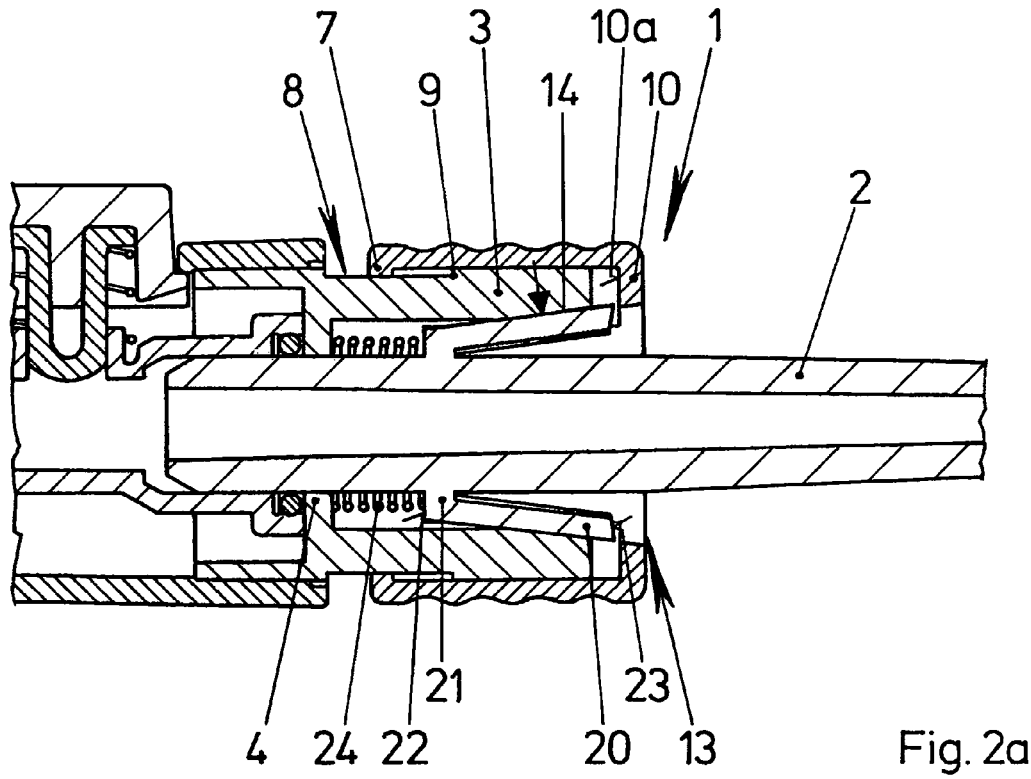
Figure 2B:
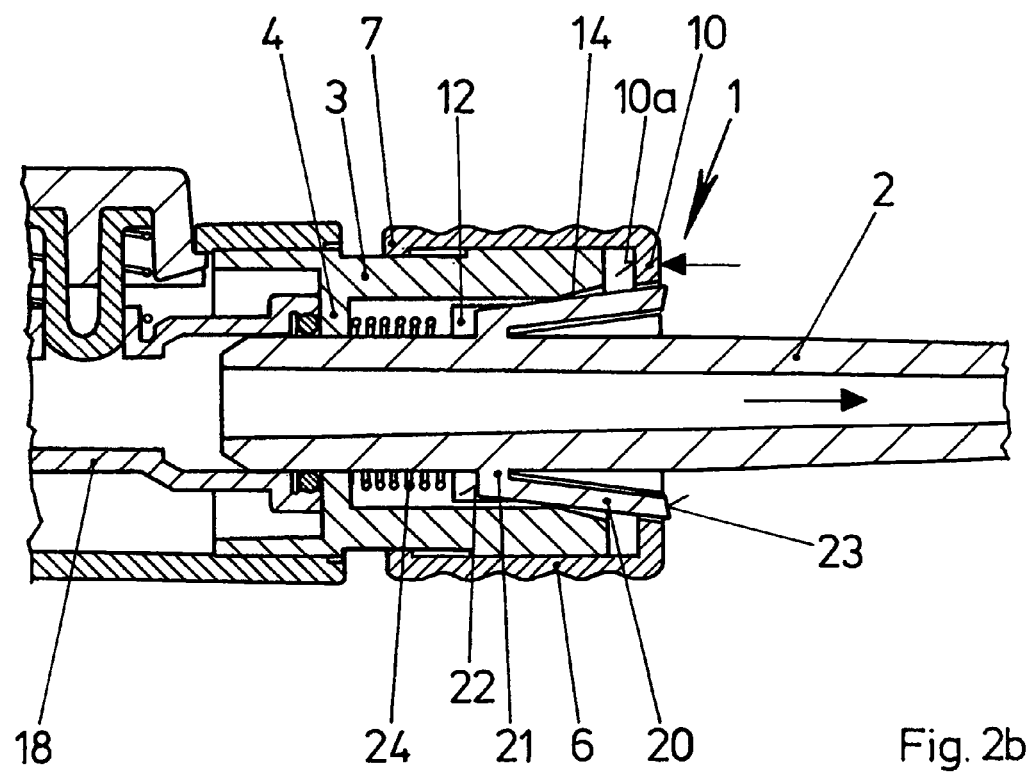

To release the connection, a procedure according to FIGS. 2a and 2b takes place. The sleeve 6 slides back onto the hollow cylinder 3 and takes the nozzle tube 2 with it while the cylindrical spring 24 is compressed.

In the process, the lugs 20 come in contact with the truncated cone 14 which forces them towards the inside while the lug ends also move inwards so that the end surfaces 23 leave the locking surfaces 10a of the flange 10 so that the recess engagement is eliminated. When this happens—as is shown in FIG. 1b—the nozzle tube 2 shoots out of the jack 1 under the effect of the relaxing spring 24. The spring 24 again comes into contact with the face 12a of the walls 12 and thereby slides the sleeve 6 back into its basic position.

To establish the connection between the nozzle tube 2 and the jack 1, the nozzle tube 2 merely has to be inserted into the jack 1. For releasing the connection, the sleeve 6 merely has to be slid back.

LIST OF REFERENCE NUMBERS

1. Jack
2. Nozzle tube
3. Hollow cylinder
4. Base
5. Opening
6. Sleeve
7. Collar
8. Outer groove
9. Stop
10. Flange
10a. Locking surface
11. Protrusions
12. Walls
12a. Face
13. Channel
14. Truncated cone
15. Extension
16. Accommodation
17. Hand piece
18. Pipe
19. Sealing ring
20. Lugs
21. Web
22. Stop surface
23. End surface
24. Spring

The invention claimed is:
1. A releasable plug connection, which is either in a connected or released state, comprising:
a jack, and
a plug,
wherein, in the connected state, the plug is inserted into the jack and held in it by a lug standing out with respect to the plug at an acute angle, for the purpose of which the lug is connected with the plug in a radially spring loaded manner and contacts a locking surface formed on the jack, as a result of which sliding back of the plug out of the jack is prevented,
wherein the locking surface extends largely radially to the longitudinal axis of the jack and the plug, and the jack consists of a hollow cylinder and a sleeve surrounding part of the hollow cylinder that can be displaced by relative axial sliding with respect to each other to a limited extent in an axial direction,
wherein the locking surface is formed on a flange at one end of the sleeve, and the hollow cylinder has a contact point for the lug which cooperates with the lug on pushing together of the hollow cylinder and the sleeve against the force of a spring acting in the axial direction, and
wherein the plug, to which the lug is connected, and the lug move relative to the jack so that the lug contacts the contact point and is pushed from the locking surface in a radial direction by sliding on the contact point to allow withdrawal of the plug from the jack.

2. The releasable plug connection according to claim 1, wherein the contact point is formed by a circumferential edge of said hollow cylinder, followed by an inclined surface of said hollow cylinder.

3. The releasable plug connection according to claim 1, wherein the plug includes a nozzle tube, and the lug stands out from the nozzle tube at the acute angle and yields under spring load in radial direction.

4. The releasable plug connection according to claim 3, wherein an end of the lug has an end surface which, in the relaxed spring state of the lug, extends parallel to the locking surface.

5. The releasable plug connection according to claim 3, wherein the lug has a web which stands out radially from the nozzle tube.

6. The releasable plug connection according to claim 3, wherein the jack consists of a hollow cylinder and a sleeve which slides on the hollow cylinder against a stop, wherein the stop defines the greatest longitudinal expansion of the jack, and wherein the sleeve has an inwardly directed flange, the side of which facing the hollow cylinder defines the locking surface.

7. The releasable plug connection according to claim 6, wherein the hollow cylinder has an inner wall which is frustoconical at one end.

8. The releasable plug connection according to claim 7, wherein the sleeve has a spring stop protruding into the hollow cylinder for the spring acting in the axial direction, and wherein the distance between the spring stop and locking surface is smaller than the length of the lug.

9. The releasable plug connection according to claim 8, wherein extensions originate from the flange in the axial direction and the spring stop is formed by the faces of these extensions, two of which form a guide for the lug.

10. The releasable plug connection according to claim 6, wherein the hollow cylinder has a base by which the spring, co-axially arranged relative to the nozzle tube, is supported.

11. The releasable plug connection according to claim 10, wherein the base of the hollow cylinder has a central opening through which the nozzle tube protrudes.

* * * * *